(12) United States Patent
Laufer

(10) Patent No.: US 9,383,328 B2
(45) Date of Patent: Jul. 5, 2016

(54) LITHOGRAPHY APPARATUS

(71) Applicant: Carl Zeiss SMT GmbH, Oberkochen (DE)

(72) Inventor: Timo Laufer, Stuttgart (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 400 days.

(21) Appl. No.: 13/967,630

(22) Filed: Aug. 15, 2013

(65) Prior Publication Data

US 2013/0343422 A1   Dec. 26, 2013

Related U.S. Application Data

(63) Continuation of application No. PCT/EP2012/001249, filed on Mar. 21, 2012.

(60) Provisional application No. 61/466,074, filed on Mar. 22, 2011.

(30) Foreign Application Priority Data

Mar. 22, 2011   (DE) .......................... 10 2011 005 885

(51) Int. Cl.
*G01N 25/16* (2006.01)
*G03F 7/20* (2006.01)

(52) U.S. Cl.
CPC .............. *G01N 25/16* (2013.01); *G03F 7/7085* (2013.01); *G03F 7/70825* (2013.01); *G03F 7/70858* (2013.01)

(58) Field of Classification Search
CPC ............ G03F 7/70825; G03F 7/70833; G03F 7/70891; G03F 7/7085; G03F 7/70858; G03F 7/70875; G03F 7/7095; G01N 25/16

USPC ...................................................... 374/55, 56
See application file for complete search history.

(56) References Cited

U.S. PATENT DOCUMENTS

| | | | |
|---|---|---|---|
| 7,755,742 B2 | 7/2010 | Cornelissen et al. | |
| 2003/0010902 A1 | 1/2003 | Hof et al. | |

(Continued)

FOREIGN PATENT DOCUMENTS

| | | | |
|---|---|---|---|
| CN | 1949081 A | 4/2007 | |
| CN | 101364049 A | 2/2009 | |

(Continued)

OTHER PUBLICATIONS

Chinese office action, with English translation thereof, for CN Appl No. 201280014780.4, dated Apr. 3, 2015.

(Continued)

*Primary Examiner* — Lisa Caputo
*Assistant Examiner* — Philip Cotey
(74) *Attorney, Agent, or Firm* — Fish & Richardson P.C.

(57) ABSTRACT

A lithography apparatus comprises a structural element, a sensor having a detection region for detecting a physical quantity in at least one detection direction with respect to the structural element, and a sensor receptacle for mounting the sensor to the structural element, wherein the sensor is arranged in such a way that the maximum displacement of the detection region in the detection direction relative to the structural element is not greater than the maximum displacement of the detection region in the detection direction in the case of an arrangement of the sensor orthogonally with respect thereto.

20 Claims, 6 Drawing Sheets

(56) References Cited

U.S. PATENT DOCUMENTS

| | | |
|---|---|---|
| 2004/0146336 A1 | 7/2004 | Maul et al. |
| 2005/0094155 A1 | 5/2005 | Hill et al. |
| 2006/0187428 A1 | 8/2006 | Bleeker et al. |
| 2007/0047876 A1 | 3/2007 | Kwan et al. |
| 2007/0081141 A1 | 4/2007 | Cornelissen et al. |
| 2007/0195296 A1 | 8/2007 | Van Der Pasch et al. |
| 2008/0024748 A1* | 1/2008 | Zaal ............... G03F 7/70516 355/72 |
| 2008/0316460 A1 | 12/2008 | Loopstra et al. |
| 2008/0319569 A1 | 12/2008 | Loopstra et al. |
| 2009/0231561 A1 | 9/2009 | Arai |
| 2011/0232878 A1* | 9/2011 | Jacobs ............... F28D 15/04 165/104.26 |
| 2013/0189802 A1* | 7/2013 | Tromp ............... G03F 7/707 438/14 |

FOREIGN PATENT DOCUMENTS

| | | |
|---|---|---|
| CN | 101762990 A | 6/2010 |
| DE | 101 34 387 | 1/2003 |
| DE | 102 59 186 | 7/2004 |
| DE | 10259186 A1 | 7/2004 |
| JP | H10-019513 A | 1/1998 |
| JP | 2002-075827 A | 3/2002 |
| JP | 2004-153092 A | 5/2004 |
| JP | 2007-129212 A | 5/2007 |
| JP | 2007-266581 A | 10/2007 |
| JP | 2009-016820 A | 1/2009 |
| WO | WO 2005/081060 | 9/2005 |
| WO | WO 2009/011356 A1 | 1/2009 |

OTHER PUBLICATIONS

The International Search Report for corresponding PCT Appl No. PCT/EP2012/001249, dated Sep. 26, 2012.

Japanese office action, with translation thereof, for JP Appl No. 2014-500282, dated Aug. 27, 2014.

Taiwanese Office Action, with translation thereof, for TW Appl No. 101109637, dated Apr. 17, 2015.

Japanese Office Action with English translation thereof for JP Appl. No. 2014-500282, 4 pages, dated Jul. 30, 2015.

* cited by examiner

LITHOGRAPHY APPARATUS

CROSS-REFERENCE TO RELATED APPLICATIONS

This application is based upon and claims the benefit of priority from the prior German Patent Application No. 10 2011 055 885.0, filed on Mar. 22, 2011, the entire contents of which are incorporated herein by reference.

FIELD OF THE INVENTION

The invention relates to a lithography apparatus comprising a sensor mounted with the aid of a sensor receptacle on a structural element of the lithography apparatus.

RELATED ART

Such a lithography apparatus is used, for example, during the production of integrated circuits or ICs in order to image a mask pattern in a mask on a substrate such as e.g. a silicon wafer. In this case, by way of example, a light beam generated by an illumination apparatus is directed through the mask onto the substrate. An exposure lens which can consist of a plurality of optical elements, such as e.g. mirrors and/or lens elements, is provided for focusing the light beam on the substrate. The individual optical elements are to be positioned as exactly as possible with regard to their orientation, since even slight deviations in the position of the optical elements can lead to an impairment of the imaged pattern, which can lead to defects in the integrated circuits produced. For this reason, lithography apparatuses often comprise sensors for detecting the position of the optical elements, and also actuators which allow the position of the optical elements to be readjusted.

The published patent application DE 101 34 387 A1 discloses in this context an exposure lens for semiconductor lithography comprising a plurality of optical elements arranged on a load-bearing structure, and a measuring structure, on which position sensors are arranged which detect the positions of the optical elements. The measuring structure is embodied independently of the load-removing structure, as a result of which a high accuracy of the measurements is intended to be made possible.

The published patent application DE 102 59 186A1 discloses an apparatus for receiving measuring instruments, in particular interferometers, which is formed from a plurality of interconnected structural elements having a very low coefficient of thermal expansion.

Furthermore, WO 2005/081060 A2 discloses an optical arrangement comprising at least one optical element which is movable in at least two degrees of freedom, and at least one actuator for adjusting the optical element, and also a sensor, which is arranged on the diagonally opposite side of the actuator with respect to the optical element.

One problem that arises in lithography apparatuses is the temperature-dictated expansion (i.e., the expansion caused by temperature changes) of structural and optical elements. On account of the heat arising during operation of the exposure apparatus, temperature changes can occur at the lithography apparatus, which temperature changes lead to a thermal expansion of structural and optical elements. This can be counteracted to a certain degree by a temperature regulation, e.g. via a cooler, which keeps the temperature in the lithography apparatus as constant as possible. Furthermore, DE 101 34 387 A1 already cited above proposes manufacturing the measuring structure, which serves as a reference frame, from a material having as low a coefficient of thermal expansion as possible, such as, e.g. Invar or Zerodur.

However, with increasing miniaturization of the structures to be imaged, the requirements made of the sensor accuracy also increase.

SUMMARY OF THE INVENTION

It is therefore an object of the present invention to provide a lithography apparatus, comprising a sensor whose measurement results are influenced or corrupted as little as possible by temperature changes in the lithography apparatus.

In accordance with one aspect of the invention, this object is achieved via a lithography apparatus, comprising a structural element, a sensor having a detection region for detecting a physical quantity in at least one detection direction with respect to the structural element, and a sensor receptacle for mounting the sensor to the structural element, wherein the sensor is arranged in such a way that, upon a change in the temperature of the sensor receptacle, the maximum displacement of the detection region in the detection direction relative to the structural element is not greater than the maximum displacement of the detection region in the detection direction in the case of an arrangement of the sensor orthogonally with respect thereto, or in other words in the case of an arrangement in which the sensor is rotated by 90°. In accordance with one aspect of the invention, this object is achieved via a lithography apparatus, comprising a structural element, a sensor having a detection region for detecting a physical quantity in at least one detection direction with respect to the structural element, and a sensor receptacle for mounting the sensor to the structural element, wherein the sensor is arranged in such a way that, upon a change in the temperature of the sensor receptacle, the displacement of the detection region in the detection direction relative to the structural element is not greater than the displacement of the detection region orthogonally with respect to the detection direction relative to the structural element.

This ensures that changes in the temperature of the sensor receptacle affect the measurement result of the sensor to a lesser extent, such that a higher measurement accuracy can be achieved.

Upon a change in the temperature of the sensor receptacle, in this case the detection region is substantially not displaced in the detection direction relative to the structural element, which can mean, in particular, that upon a change in the temperature of the sensor receptacle by a predetermined temperature change value, the detection region is displaced in the detection direction by not more than a predetermined absolute value of displacement relative to the structural element. In this case, the predetermined temperature change value can be 10 mK, preferably 100 mK, particularly preferably 1 K. The predetermined absolute value of displacement can be, for example, 100 nm, preferably 10 nm, particularly preferably 1 nm, and in particular preferably 0.1 nm.

The sensor can be arranged in such a way that the detection direction of the sensor is substantially orthogonal, that is to say within an orthogonality range orthogonal with respect to a thermal expansion direction of the sensor receptacle at the detection region of the sensor upon a change in the temperature. By way of example, the detection direction of the sensor can form with the thermal expansion direction of the sensor receptacle at the detection region an angle of 90°±10°, preferably of 90°±1°, particularly preferably 90°±0.1°, and in particular preferably 90°±0.01°. The closer this angle is to 90°, the smaller the measurement error on account of the thermal expansion of the sensor receptacle.

The detection region of the sensor can be arranged at a location of the sensor receptacle which, upon a predetermined change in the temperature, is not displaced in any direction by more than a predetermined absolute value of expansion relative to the structural element. In other words, the detection region of the sensor can therefore be arranged at a temperature-invariant point. A temperature-invariant point is a point at the surface of the sensor receptacle which, upon a uniform change in the temperature of the sensor receptacle, is not displaced relative to the structural element. As in the case mentioned above, here the predetermined temperature change value can be, for example, 10 mK, preferably 100 mK, particularly preferably 1 K, and the predetermined absolute value of displacement can be, for example, 100 nm, preferably 10 nm, particularly preferably 1 nm, and in particular preferably 0.1 nm. As a result of the arrangement of the detection region of the sensor at the temperature-invariant point, too, the influence of temperature changes on the measurement result can be minimized.

The lithography apparatus can comprise a first sensor having a first detection region for detecting a physical quantity in a first detection direction, and a second sensor having a second detection region for detecting a physical quantity in a second detection direction, wherein the first sensor is arranged in such a way that, upon a change in the temperature of the sensor receptacle, the first detection region is substantially not displaced in the detection direction relative to the structural element, and the second sensor is arranged in such a way that, upon a change in the temperature of the sensor receptacle, the second detection region is substantially not displaced in the detection direction relative to the structural element. Consequently, a lithography apparatus is provided in which two sensors are arranged on a sensor receptacle, such that a more space-saving arrangement is made possible. Furthermore, in the case of this arrangement, it is advantageous that the number of sensor receptacles can be reduced. Furthermore, the influence of temperature changes on the measurement results of both sensors is minimized.

The first detection direction and the second detection direction of the two sensors can be substantially orthogonal, that is to say within an orthogonality range orthogonal with respect to one another, that is to say e.g. form an angle of 90°±10°, preferably of 90°±1°, particularly preferably 90°±0.1°, and in particular preferably 90°±0.01°. Consequently, a sensor arrangement can be provided which detects the position of an optical element in the lithography apparatus with respect to two degrees of freedom.

The first and/or the second sensor can be arranged in a region of the sensor receptacle which, upon a change in the temperature by a predetermined temperature change value, is not displaced in any direction by more than a predetermined absolute value of expansion relative to the structural element. In this case, the predetermined temperature change value and the predetermined absolute value of expansion can be as mentioned above. Furthermore, a sensor can be provided which is adapted to detect a physical quantity in two detection directions, wherein the sensor is arranged at a position of the sensor receptacle which, upon a change in the temperature, is displaced direction-independently by not more than a predetermined absolute value of expansion relative to the structural element. In this case, the predetermined temperature change value and the predetermined absolute value of expansion can be as mentioned above. Such a sensor enables a sensor arrangement which detects the position of an optical element in the lithography apparatus with respect to two degrees of freedom. As a result of the arrangement of the detection region at the temperature-invariant point, the influence of temperature changes on the measurement result can be minimized.

The sensor receptacle can be thermally decoupled from the structural element. This enables an arrangement in which the sensor receptacle has a different, in particular a greater, coefficient of thermal expansion than the structural element.

The structural element can be a measuring frame. Such a measuring frame can serve as a reference for the detection of the position of optical elements in the lithography apparatus, and is, in particular, stationary in relation to temperature changes, vibrations and the like.

The sensor can be embodied as a position sensor which detects the position of an optical element of the lithography apparatus. By way of example, the sensor can comprise a photodetector which detects an encoder pattern on an optical element.

Further exemplary embodiments will be explained with reference to the accompanying drawings.

BRIEF DESCRIPTION OF THE DRAWINGS

Unless indicated otherwise, identical reference signs in the figures designate identical or functionally identical elements.

EMBODIMENTS OF THE INVENTION

First Exemplary Embodiment

Figure 1:
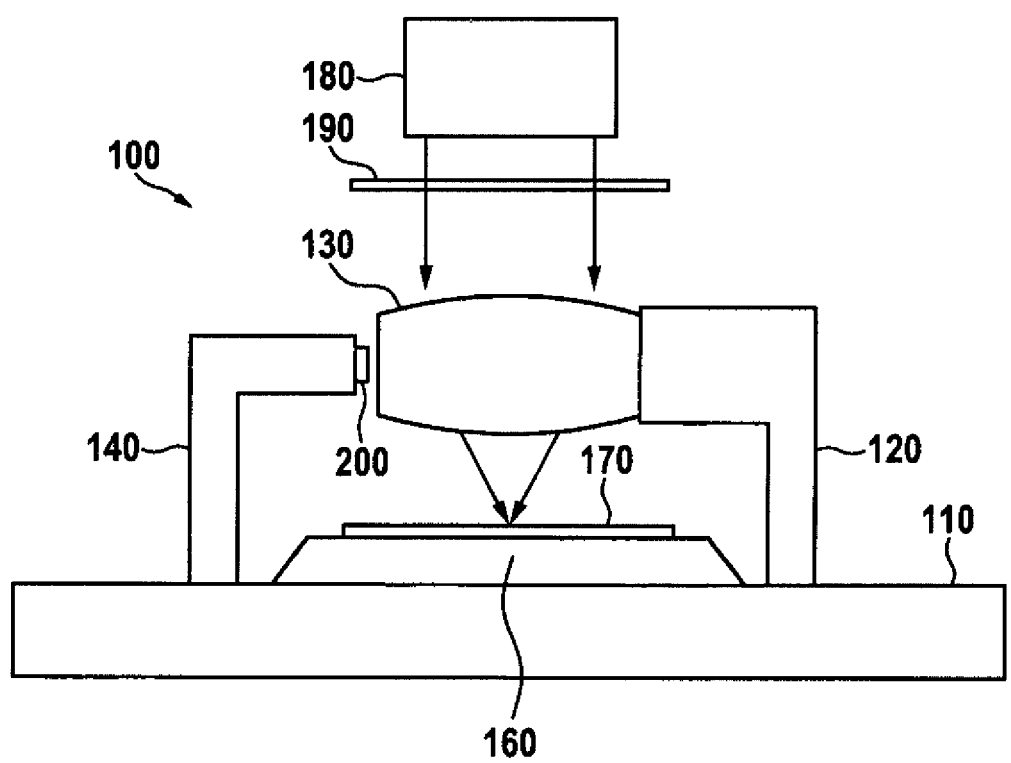
FIG. 1 shows a schematic view of a lithography apparatus in accordance with a first exemplary embodiment.

FIG. 1 shows a schematic view of a lithography apparatus 100 in accordance with a first exemplary embodiment. This lithography apparatus 100 comprises a baseplate 110, on which a holding frame 120 for mounting at least one optical element 130 and a measuring frame 140 for mounting a sensor arrangement 200 are provided. The lithography apparatus 100 typically comprises a plurality of optical elements. In FIG. 1, however, only one optical element 130 is illustrated by way of example, in order to schematically elucidate the functioning of the lithography apparatus 100.

In the example illustrated, a wafer receptacle (wafer holder) 160 is provided below the optical element 130, in which wafer receptacle a wafer 170, e.g. a silicon wafer, can be received. The wafer receptacle 160 can be embodied as a step-and-scan system, for example, which moves the wafer 170 during the exposure and also in the exposure pauses step-by-step relative to the baseplate 110.

The optical element 130 illustrated in FIG. 1 comprises a lens element system, that is to say a combination of lens elements or a combination of lens elements and mirrors. An illumination apparatus 180 is provided above the optical element 130, and generates a radiation beam for the exposure of the wafer 170. The light beam emerging from the illumination apparatus 180 passes through a mask 190 which is merely illustrated schematically here, and is concentrated by the lens element system of the optical element 130, such that a pattern provided in the mask 190 is imaged on the wafer 170 in demagnified fashion. As an alternative to this embodiment, the optical element 130 can also be embodied as a mirror arrangement, that is to say as a combination of mirrors, or else as a combination of mirrors and lens elements, which concentrates the light emerging from the illumination apparatus 180.

In order to ensure a high optical resolution, the optical element 130 has to be arranged precisely at the optimum position and in an optimum orientation during each exposure process. For this purpose, a plurality of sensors are provided which detect the orientation of the optical element 130 with respect to all six degrees of freedom. The six degrees of freedom comprise translational movements along the three spatial axes and rotational movements about the three spatial axes. In the present case, for the sake of simplicity, the illustration merely shows a sensor arrangement 200 in which one sensor is provided, which detects the position of the optical element 130 with respect to one degree of freedom.

The measuring frame 140 is a structural element of the lithography apparatus 100 and serves as an independent reference frame, which is provided independently of the holding frame 120. The measuring frame 140 can be mounted on the baseplate 110 for example via a spring mechanism and/or a damper. Consequently, vibrations which occur during operation are damped, and an almost complete mechanical decoupling between the measuring frame 140 and the holding frame 120 is made possible. This damping can be an active damping.

Figure 2:
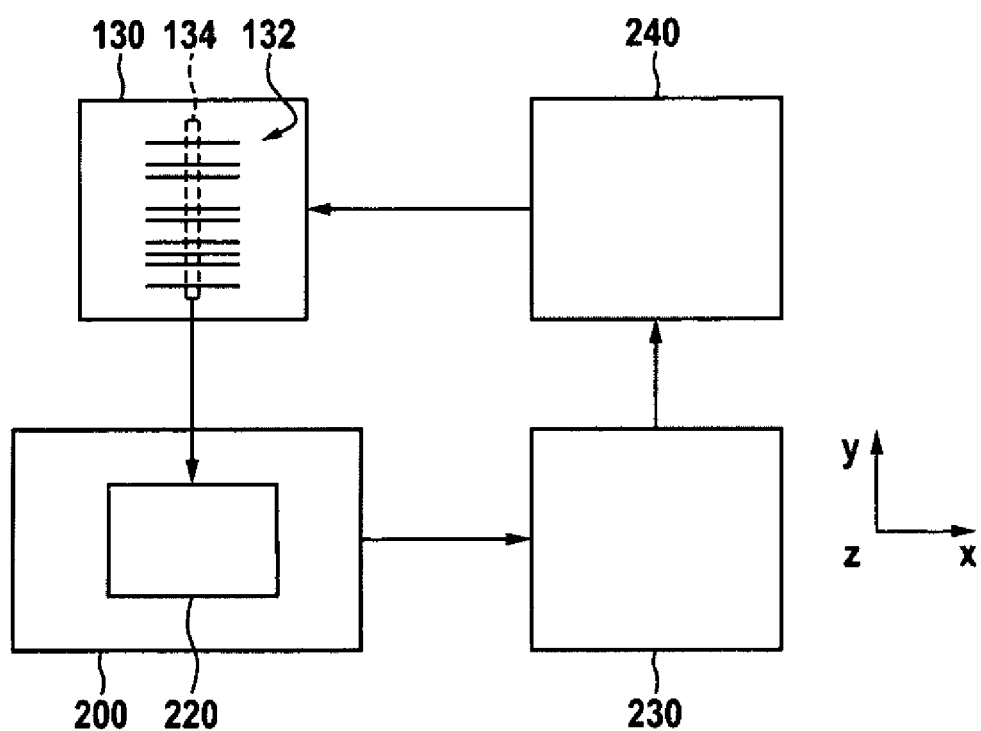
FIG. 2 schematically illustrates the detection and regulation of the position of an optical element.

FIG. 2 schematically illustrates the detection and regulation of the position of the optical element 130.

An encoder pattern 132 is provided on that side of the optical element 130 which faces the sensor arrangement 200. The encoder pattern 132 consists, for example, of a sequence of dark and light bars, similar to a barcode or a line grating. A sensor 220 arranged on the sensor arrangement 200 detects the encoder pattern 132 in a pattern region 134. The sensor 220 can be embodied as a photodetector, for example, and have in particular an array of photodiodes arranged along a detection direction of the sensor 220. The photodiodes convert light reflected from the pattern region 134 into an electrical signal, which is processed by components (not illustrated more specifically) in the sensor 220, and pass the resulting sensor signal to an evaluation device 230.

On the basis of the sensor signal, the evaluation device 230 determines the position of the optical element 130 in the detection direction relative to the sensor 220. In the example illustrated in FIG. 2, the detection direction is the y-direction. Furthermore, the evaluation device 230 outputs a control signal to an actuator 240 which regulates the position of the optical element 130 in the detection direction. Consequently, the sensor 220, the evaluation device 230 and the actuator 240 form a regulation system that regulates the position of the optical element 130 with respect to one degree of freedom, that is to say here translationally in the y-direction. Corresponding regulation systems are provided for all six degrees of freedom, such that the optical element 130 can be oriented precisely with respect to all six degrees of freedom. Furthermore, corresponding regulation systems can be provided for a plurality of optical elements 130 arranged in the lithography apparatus 100. If the lithography apparatus comprises, for example five mirrors for concentrating the light emerging from the illumination apparatus, then it is therefore possible to provide a total of 30 of the regulation systems described with a corresponding number of mirror position sensors.

It should be taken into consideration that the encoder pattern need not necessarily be provided on the optical element 130 itself, but rather can also be provided on a component fixedly connected to the optical element 130, such as e.g. a frame for receiving the optical element. However, it is advantageous if the encoder pattern is provided as near as possible to the optical element 130, in order to avoid measurement errors on account of thermal expansions to the greatest possible extent.

The sensor 220 responds to changes in the position of the optical element 130 in a movement direction, namely the y-direction in FIG. 2. This direction in which the sensor 220 is sensitive, is also designated hereinafter as "detection direction". By contrast, the sensor 220 is comparatively insensitive with regard to movements of the optical element 130 in directions orthogonal with respect to the detection direction, that is to say for example in the x-direction in FIG. 2. If the optical element 130 moves in the x-direction, for example, then although the pattern region 134 on the encoder pattern 132 is displaced in the opposite direction with respect to the encoder pattern 132, that is to say in the negative x-direction in the example illustrated, this does not lead to a change in the detected pattern such that the sensor signal output by the sensor 220 also remains unchanged.

Figure 3:
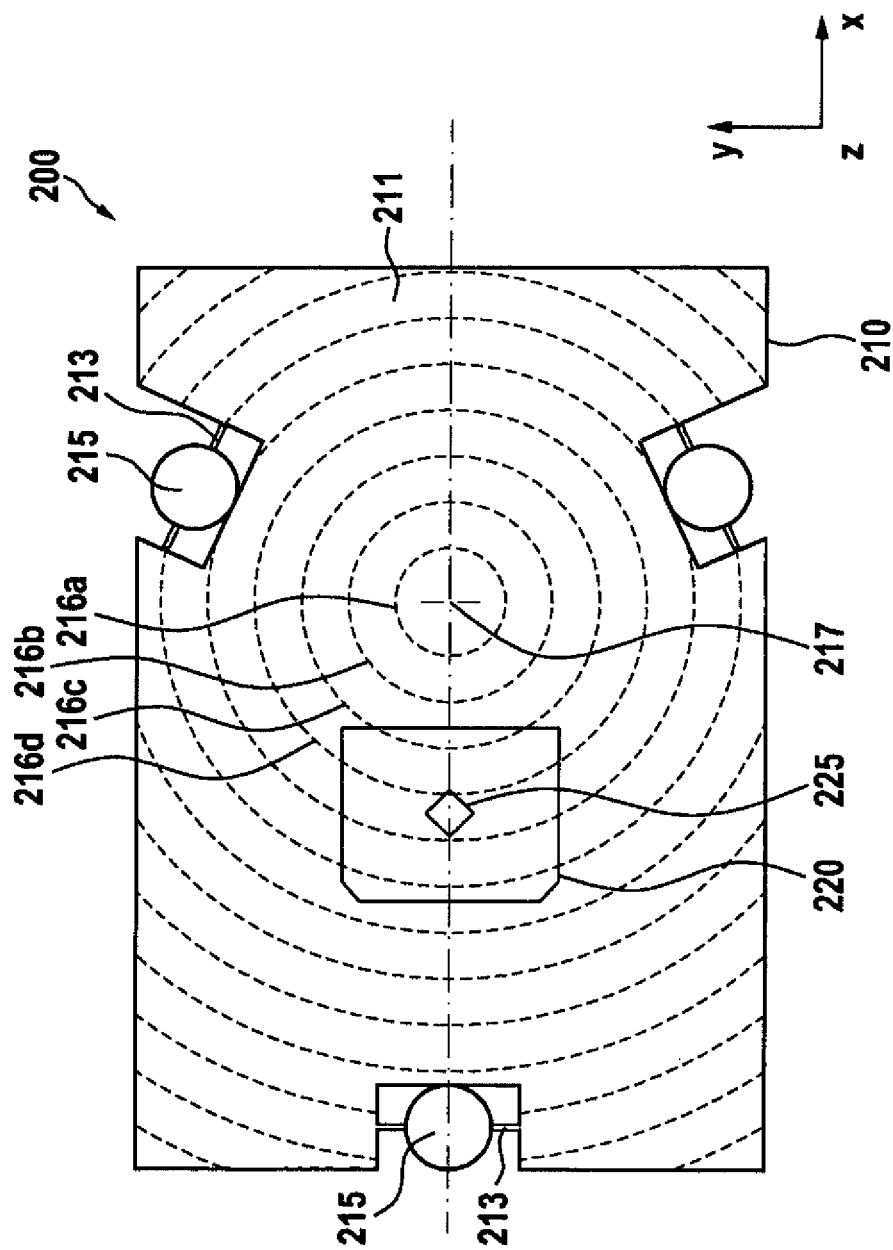
FIG. 3 shows a plan view of the sensor arrangement in accordance with a first exemplary embodiment.

FIG. 3 shows a plan view of the sensor arrangement 200.

The sensor arrangement 200 comprises a sensor receptacle (sensor holder) 210 and a sensor 220 received in or mounted on the sensor receptacle 210. The sensor receptacle 210 can have, for example, a rectangular, plate-shaped baseplate 211 which can be, for example, approximately 140 mm long and 100 mm wide. The sensor 220 can be fixed, e.g. screwed, on the baseplate 211, for example, or else be fixed in a cutout provided in the baseplate 211. In the baseplate 211, a through-hole (not illustrated) can furthermore be provided though which connections for the sensor 220 are led to the rear side of the sensor receptacle 210.

The sensor receptacle 210 can be produced from steel, for example, and has, in the same way as the sensor 220 a higher coefficient of thermal expansion than the measuring frame 140, which is manufactured, for example, from Invar or a suitable ceramic having a low coefficient of thermal expansion. If the sensor 220 were fixed areally on the measuring frame 140 then the different coefficients of thermal expansion would lead to high mechanical stresses and to deformations of the sensor 220 which can impair the measurement result. For this reason, the sensor 220 is fixed to the measuring frame 140 via a thermally decoupled mounting. For this purpose, quadrangular cutouts are provided at three locations of the sensor receptacle 210. A respective leaf spring 213 is provided within the cutouts. In the example illustrated, the leaf springs 213 extend from a region in the center of one side of the quadrangular cutout to the opposite side. The leaf springs 213 are strip-shaped and manufactured from the same material as the sensor receptacle 210. The entire sensor receptacle 210 is therefore monolithic in the present example. Cylindrical thickenings 215 are provided in a region in the center of the leaf springs 213. The sensor receptacle 210, the leaf springs 213 and the thickenings 215 can be manufactured integrally from the same material, as a result of which drift can be avoided. It should be taken into consideration that the illustrated form of the sensor receptacle 210 and the arrangement of the leaf springs 213 in the sensor receptacle 210 are merely by way of example.

Fixing mechanisms (not shown in the drawings) are provided at the thickenings 215 by which fixing mechanisms the sensor receptacle 210 can be fixed, e.g. screwed, to the measuring frame 140. The sensor receptacle 210 is therefore firmly fixed to the measuring frame 140 at three locations.

During the operation of the lithography apparatus 100, temperature fluctuations can occur, for example on account of the heat liberated by the illumination apparatus 180. Furthermore, the sensor 220 also constitutes an additional heat source during operation, which primarily heats the sensor receptacle 210. The material of the measuring frame 140 has such a low coefficient of thermal expansion that its position can be regarded as fixed over the temperature range that occurs during operation. It therefore serves as a reference frame for the measurements of the positions of the optical elements. By contrast, the sensor receptacle 210 expands relative to a reference point at the sensor frame 140. This is clarified via the expansion lines 216a, 216b, 216c, etc. illustrated in FIG. 3, which are situated at the distance $\Delta x$, $2\cdot\Delta x$, $3\cdot\Delta x$, etc. from a temperature-invariant point 217 of the sensor receptacle 210. Each of these circular expansion lines 216 marks a linear region which, upon a homogeneous rise in the temperature of the sensor receptacle 210 recedes radially from the temperature-invariant point 217 by the same absolute value. Upon a homogeneous change in the temperature, these regions of identical displacement extend as lateral surfaces of cylinders through the three-dimensional sensor receptacle 210. The expansion lines 216a, 216b, 216c, etc. represent the lines of intersection of the lateral surfaces of cylinders with the surface of the sensor receptacle 210.

The points along the expansion line 216a are therefore displaced from the temperature-invariant point 217 by an absolute value $\Delta x$ of expansion upon a temperature increase $\Delta T$, the points along the expansion line 216b are displaced from the temperature-invariant point 217 by double the absolute value of expansion, $2\cdot\Delta x$, upon a homogeneous temperature increase $\Delta T$, etc., wherein it is assumed that the distance between the temperature-invariant point 217 and the line 216a is the same as the distance between the lines 216a and 216b.

A substantially circular region around the temperature-invariant point 217 within which the displacement of the sensor 220 with respect to the temperature-invariant point upon a specific change in the temperature is below a predetermined absolute value $\Delta x$ of expansion can be regarded as a substantially temperature-invariant region. In the example illustrated in FIG. 3, the absolute value $\Delta x$ of expansion upon a temperature increase $\Delta T$ of 3 K can be approximately 0.3 µm, for example. Accordingly, the points on the expansion line 216a after the temperature increase lie approximately 0.3 µm further away from the temperature-invariant point 217, the points on the expansion line 216b lie 0.6 µm further away, etc.

Since the fixing mechanisms are firmly fixed to the measuring frame 140, relative displacements occur between them and the expanding sensor receptacle 210, the relative displacements being compensated for by the leaf springs 213. The leaf springs 213 flex slightly inward upon an expansion of the sensor receptacle 210. In this case, a spring force arises which acts perpendicular to the leaf springs 213 into the interior of the sensor receptacle 210. The temperature-invariant point 217 is that point at the surface of the sensor receptacle 210 which, upon a uniform change in the temperature of the sensor receptacle 210, is not displaced relative to the structural element 140.

The encoder pattern is detected at the measuring point of the sensor 220. Since the detection is effected by photodetectors which have specific dimensions, and are therefore not punctiform (point-shaped), the measuring point corresponds to a detection region 225 in which the photodetectors for detecting the encoder pattern are arranged. The detection region 225 is merely indicated schematically in FIG. 3 and does not necessarily correspond to the actual expansion of the photodetectors which contribute to the detection of the encoder pattern. The detection region 225 illustrated in FIG. 3 corresponds approximately to the size of a coupling-out window required for coupling out the optical signal. In this case, the rhomboid shape indicated in the figures corresponds to the actual detection region 225 neither in terms of its shape nor in terms of its dimensions, but rather serves merely for schematic illustration. The detection region 225 can e.g. have a greater length in the detection direction than in the directional orthogonal with respect thereto. For protecting the photodetectors, the detection region 225 can be covered with a glass plate or the like.

The detection direction of the sensor 220 illustrated in FIG. 3 is the y-direction. This detection direction is thus orthogonal with respect to the expansion direction at the location of the detection region 225, which runs perpendicular to the expansion lines 216. This ensures that the measurement is influenced as little as possible by the temperature-dictated expansion of the sensor receptacle 210. Specifically, if the position of the sensor 220 and its detection region 225 is displaced upon heating of the sensor receptacle 210 in the negative x-direction, then although the pattern region 134 on the optical element 130 is also displaced in the x-direction, the detection of the encoder pattern is not influenced by this, since the expansion of the encoder pattern in the x-direction is greater than the maximum temperature-dictated expansion of the sensor receptacle 210 at the location of the sensor 220, cf. FIG. 2.

The detection region 225 of the sensor 220 is arranged at a location of the sensor receptacle 210 which, upon a predetermined change $\Delta T$ in the temperature, is displaced by not more than a predetermined absolute value of displacement in the detection direction relative to the structural element. The change $\Delta T$ in the temperature corresponds, for example, to the maximum temperature change which can occur during operation of the lithography apparatus, that is to say for example 10 mK, preferably 100 mK or particularly preferably 1 K. The maximum absolute value of displacement in the detection direction is determined in such a way that, upon a change $\Delta T$ in the temperature, the displacement in the detection direction is so small that the measured value is corrupted by not more than a specific measurement error, e.g. 10%, preferably 1%, particularly preferably 0.1%, in particular preferably 0.01%. By way of example, the maximum absolute value of displacement in the detection direction can be defined as 100 nm, preferably 10 nm, particularly preferably 1 nm, in particular preferably 0.1 nm. The maximum absolute value of displacement can also be expressed in an angle by which the detection direction is permitted to deviate maximally from the expansion direction. In particular, the detection direction is substantially orthogonal with respect to the expansion direction. In other words, the detection direction is defined within a specific orthogonality range of 90°±10°, preferably of 90°±1°, particularly preferably 90°±0.1°, and in particular preferably 90°±0.01°, as orthogonal with respect to the expansion direction.

In the exemplary embodiment illustrated in FIG. 3, the sensor 220 is therefore arranged in such a way that, upon a change in the temperature of the sensor receptacle 210 or of the sensor 220, the detection region 225 is displaced in the detection direction (y-direction) relative to the measuring frame 140 to a lesser extent than the displacement in the detection direction would be if the sensor (detection direction) were arranged parallel to the expansion direction (that is to say orthogonally with respect to the arrangement shown in FIG. 3). If the sensor (detection direction) were arranged parallel to the expansion direction, then the detection direction would be the x-direction in this example. And since in this comparative case the detection direction coincides with this expansion direction at the location of the sensor, there would be a considerable displacement of the detection region 225 in the detection direction, falsifying the measurement. In other words, with the arrangement of the present embodiment, by arranging the detection direction at right angles to the expansion direction, an increase in the sensor accuracy can be achieved, compared to a sensor arrangement in which the detection direction is arranged, for example, parallel with respect to the expansion direction.

Figure 4:
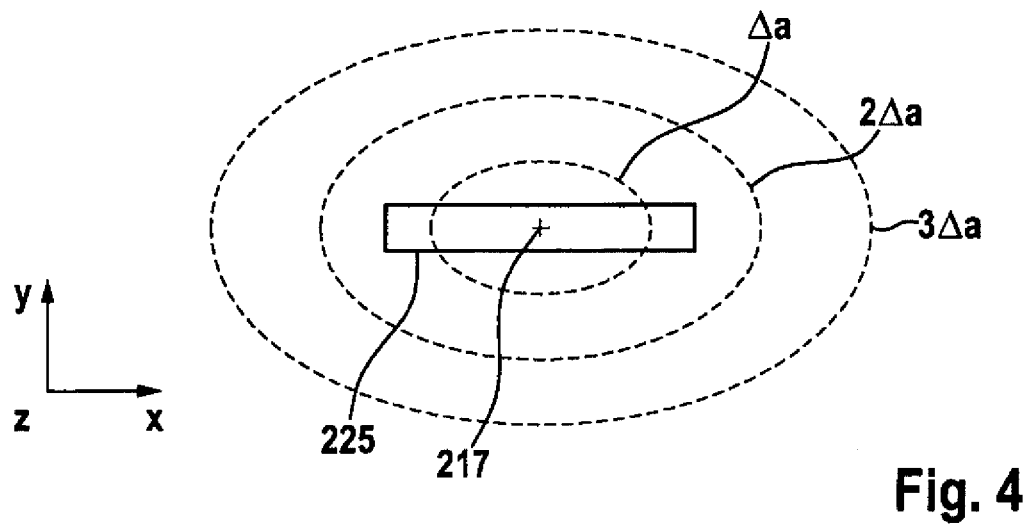
FIG. 4 shows an arrangement of a detection region in a variant of the first exemplary embodiment.

The smallest displacement relative to the measuring frame 140 is effected at the temperature-invariant point 217 described above. It is therefore advantageous to arrange the sensor 220 in such a way that the detection region 225 lies at the invariant point 217. One example of this is illustrated in FIG. 4, which illustrates the local expansion of the sensor receptacle 210 or of the sensor 220 upon a change in the temperature around the temperature-invariant point 217. In contrast to FIG. 3, the degree of the expansion in FIG. 4 is direction-dependent. To put it more precisely, upon a change in the temperature the sensor receptacle 210 expands to a greater extent in the y-direction than in the x-direction. Consequently, the dashed expansion lines in FIG. 4 also lie closer to one another in the y-direction than in the x-direction.

In the example illustrated in FIG. 4, the sensor 220 is arranged in such a way that the strip-shaped detection region 225 is arranged substantially parallel to the direction of smaller expansion, that is to say parallel to the x-direction. In this case, the maximum displacement of the detection region 225 relative to the measuring frame 140 is effected at the two ends of the strip-shaped detection region 225, wherein the displacement at the right-hand end of the detection region 225 is approximately 1.5 Δa in the +x-direction and the displacement at the left-hand end of the detection region 225 is approximately 1.5 Δa in the −x-direction. In the comparative example illustrated in FIG. 5, the sensor 220 is arranged in such a way that the strip-shaped detection region 225 is arranged substantially parallel to the direction of larger expansion, that is to say parallel to the y-direction. In this case, the maximum displacement of the detection region 225 relative to the measuring frame 140 is effected at the two ends of the strip-shaped detection region 225, wherein the displacement at the upper end of the detection region 225 is a little more than 2 Δa in the +y-direction and the displacement at the left-hand end of the detection region 225 is little more than 2 Δa in the −y-direction, that is to say more than in the case shown in FIG. 4, wherein the detection region 225 is arranged substantially parallel to the direction of smaller expansion. In other words, therefore, in the case of the arrangement shown in FIG. 4, upon a change in the temperature of the sensor receptacle 210, the maximum displacement of the detection region 225 in the detection direction (x-direction) relative to the structural element is smaller than the maximum displacement of the detection region 225 in the detection direction (y-direction) relative to the structural element in the case of the arrangement shown in FIG. 5, that is to say in the case of an arrangement of the sensor (or the detection region) orthogonally with respect to the arrangement shown in FIG. 4.

It is also directly evident that the measurement error in the case of the arrangement in FIG. 4 is smaller than in the case of an arrangement in which the sensor 220 (or the detection region 225) was rotated by an angle of 60° or 30° or 10° with respect thereto. In particular, the sensor 220, as in FIG. 4, can be arranged in such a way that, upon a change in the temperature of the sensor receptacle, the maximum displacement of the detection region 225 in the detection direction relative to the structural element is smaller than in the case of any rotation of the sensor 220. It should be noted that, by way of example, the center of gravity or the center of the detection region 225 can be chosen as reference point for a rotation of the sensor.

Figure 5:
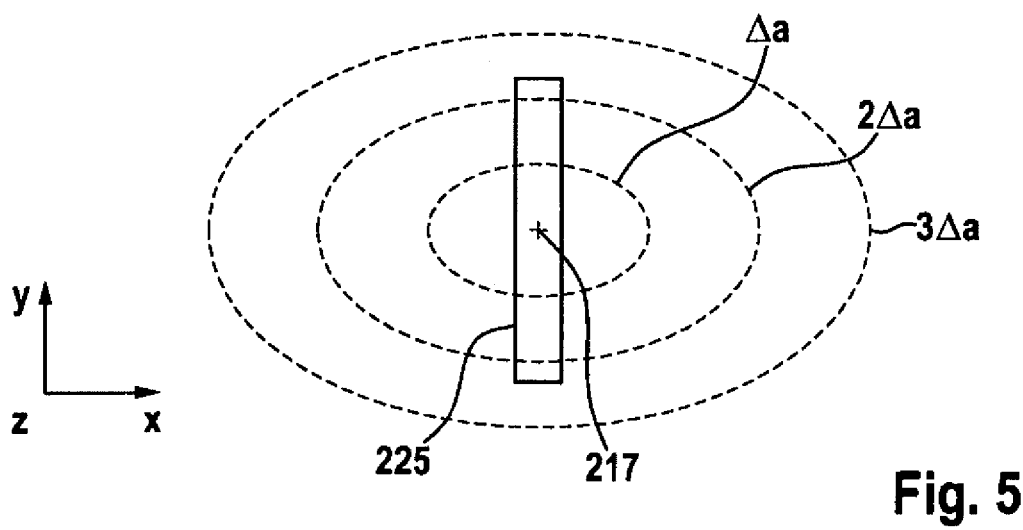
FIG. 5 shows an arrangement of a detection region in a comparative example.

As is evident from FIGS. 4 and 5, the extension or compression of the detection region 225 or of the corresponding region of the sensor receptacle 210 is greater, the more expansion lines are intersected by the detection region 225. Measurement errors can therefore be minimized by arranging the detection region 225 in such a way that it intersects as few expansion lines as possible.

It should also be noted supplementarily that, in the case of an isotropic expansion as illustrated in FIG. 3, there is no preferred arrangement of the detection region 225 at the temperature-invariant point, such that, therefore, for all orientations the condition is met that the maximum displacement of the detection region 225 in the detection direction relative to the measuring frame 140 is not greater than in the case of an arrangement of the sensor rotated by an arbitrary angle, that is to say, for example, in the case of an arrangement orthogonal with respect thereto.

It should be taken into consideration that, during the operation of the lithography apparatus 100, the temperature of the sensor receptacle 210 is not necessarily homogeneous over the entire sensor receptacle 210. The temperature of the sensor receptacle 210 can vary locally and, in particular on account of the evolution of heat in the sensor 220, can be somewhat higher in the region in which the sensor 220 is arranged than in the edge regions of the sensor receptacle 210. However, it is possible to consider such a change in temperature as a location-dependent local change in temperature and a global change in temperature which are superposed on one another. In this case, the local change in temperature is caused, for example, by the evolution of heat in the sensor 220 and the global change in temperature is a location-independent change in the temperature of the sensor receptacle 210 by a specific absolute value, which is caused, for example, by a change in the ambient temperature. In this case, a change in temperature caused by the evolution of heat in the sensor 220 generally affects the measurement result to a lesser extent if the largest change in temperature is in the detection region itself or near to the latter, since no or only an insignificant displacement of the detection region then takes place. The expression "upon a change in the temperature" can therefore be understood to mean, in particular a global change in temperature in which the temperature of the sensor receptacle changes homogeneously by a specific absolute value in a location-independent manner.

Second Exemplary Embodiment

Figure 6:
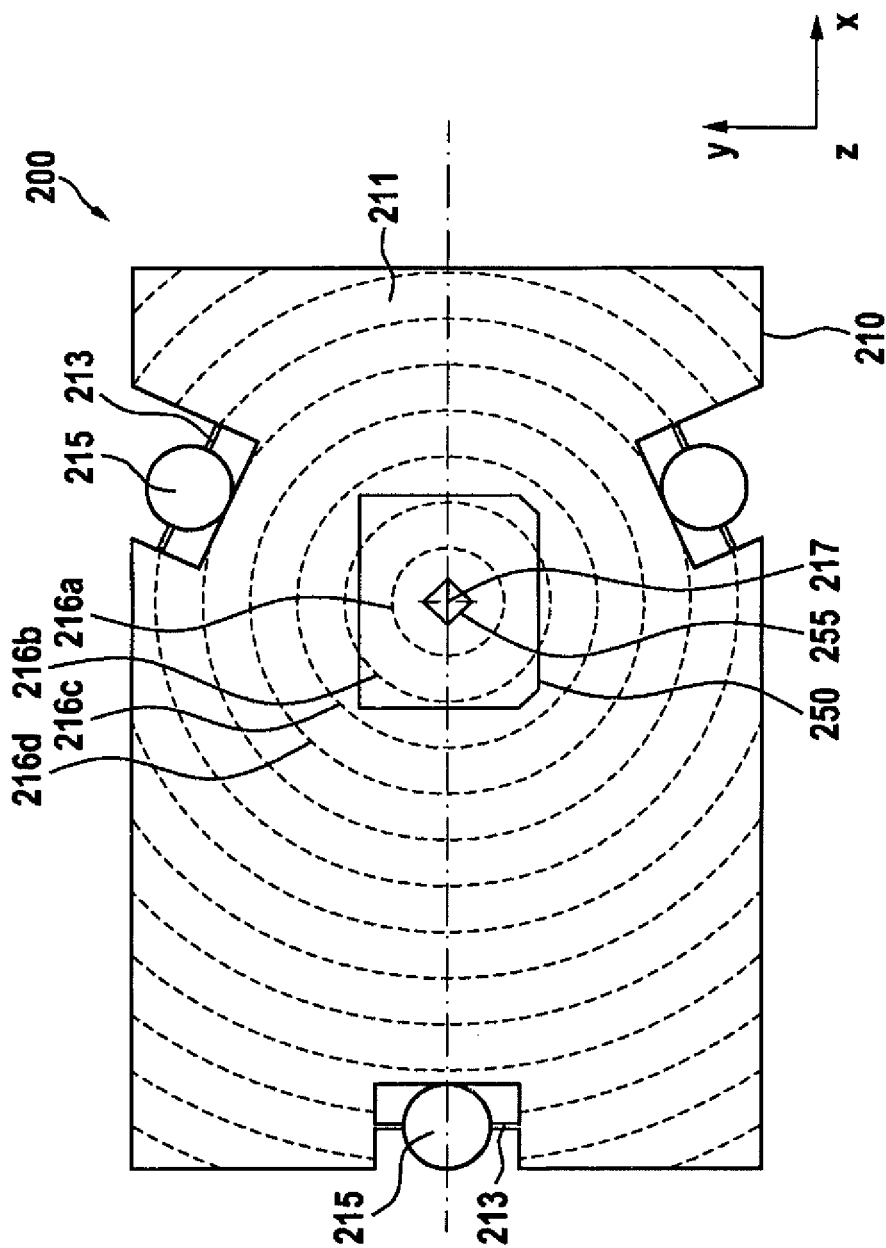
FIG. 6 shows a plan view of a sensor arrangement of a lithography apparatus in accordance with a second exemplary embodiment.

FIG. 6 shows a plan view of a sensor arrangement 200 of a lithography apparatus in accordance with a second exemplary embodiment. Elements which are structurally or functionally identical to elements of the first exemplary embodiment are identified by the same reference signs and are not explained in greater detail below. In particular, the sensor arrangement 200 shown in FIG. 6 can be used as a position sensor in the lithography apparatus 100 in FIG. 1.

In this exemplary embodiment, a sensor 250 is arranged in the sensor receptacle 210, which sensor determines the position of the optical element 130 with respect to two degrees of freedom. The sensor 250 determines the position of the optical element 130 with respect to the x-direction and the y-direction relative to the measuring frame 140. The sensor 250 therefore has two detection directions in which the sensor detects a change in the position of the optical element 130. In this exemplary embodiment, too, the sensor 250 can comprise for this purpose photodetectors which convert light reflected from the encoder pattern into an electrical signal, from which the sensor 250 generates a sensor signal. In this case, the photodetectors can be embodied as a two-dimensional array which extends over a detection region 255 and have substantially the same width in both detection directions. In this case, the encoder pattern can have two-dimensionally coded information, similar to a two-dimensional barcode. As in the first exemplary embodiment, the sensor signal is fed to an evaluation device and evaluated by the latter. In contrast to the first exemplary embodiment, the optical element 130 is moved in two directions in this case. Consequently, a regulation is provided by which the position of the optical element 130 can be regulated simultaneously with respect to two translational degrees of freedom.

The detection region 255 of the sensor 250 is arranged at the temperature-invariant point 217 or in the temperature-invariant region of the sensor receptacle 210. This ensures that, upon a temperature-dictated expansion of the sensor receptacle 210, the position of the detection region 255 does not experience any change with respect to the measurement frame 140 serving as reference. Therefore, the detection region 255 is not displaced relative to the measuring frame 140 in both detection directions.

Furthermore, the arrangement of the detection region 255 at the temperature-invariant point 217 makes it possible to provide a sensor arrangement which is particularly stable relative to temperature fluctuations, since the displacement of the temperature-invariant point is minimal even upon large changes in temperature.

It should be taken into consideration that the temperature-invariant point is not necessarily situated at the center of gravity of the sensor receptacle 210 or on the line of symmetry thereof. Moreover, the position of the temperature-invariant point is dependent on the orientation and the spring constants of the three leaf springs 213.

Third Exemplary Embodiment

Figure 7:
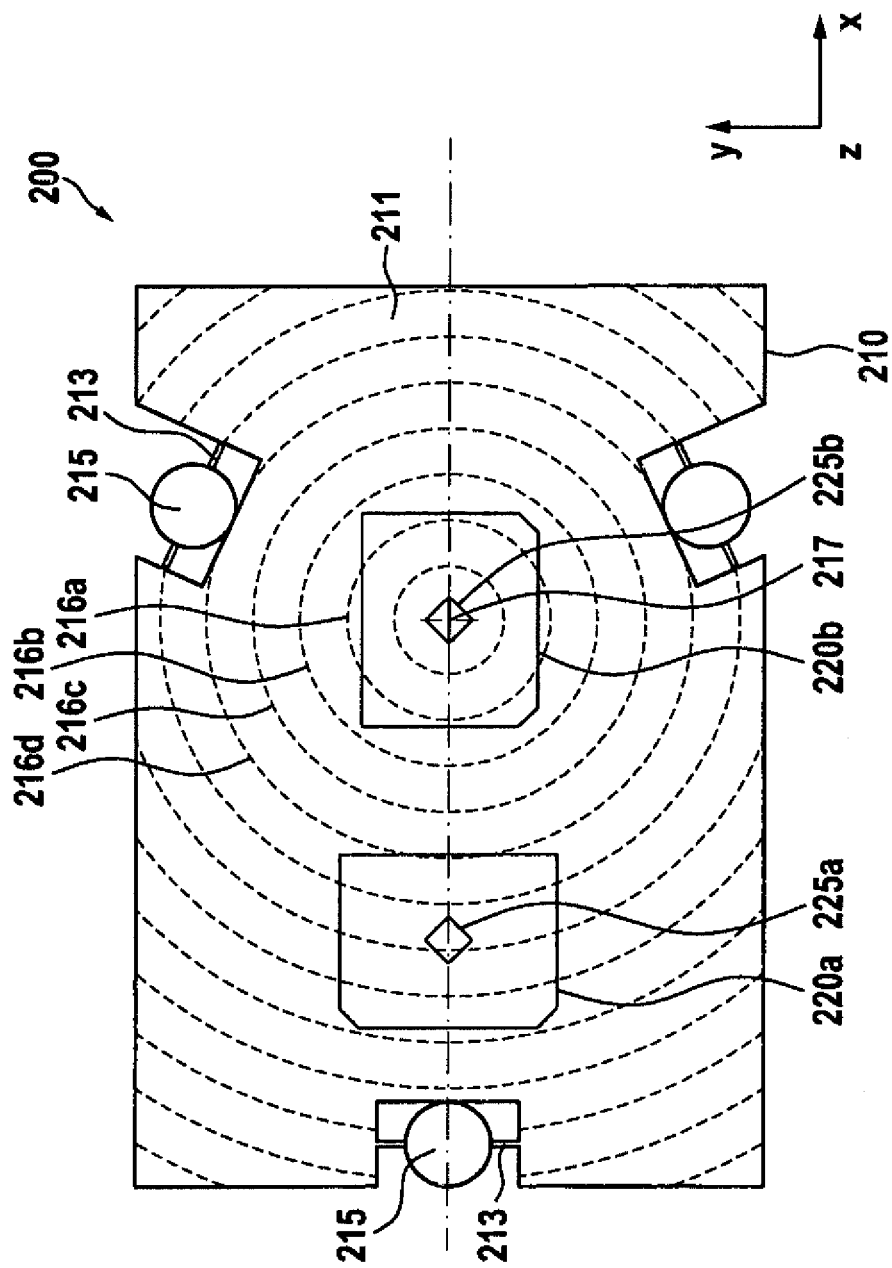
FIG. 7 shows a plan view of a sensor arrangement of a lithography apparatus in accordance with a third exemplary embodiment.

FIG. 7 shows a plan view of a sensor arrangement 200 of a lithography apparatus in accordance with a third exemplary embodiment. Elements which are structurally or functionally identical to elements of the first exemplary embodiment are identified by the same reference signs and are not explained in greater detail below. In particular, the sensor arrangement 200 shown in FIG. 7 can be used as a position sensor for detecting the position of the optical element 130 in the lithography apparatus 100 in FIG. 1.

In this exemplary embodiment, two sensors 220a and 220b are arranged on the sensor receptacle 210. The sensors 220a and 220b respectively have a detection region 225a and 225b for detecting a physical quantity. In this exemplary embodiment, the sensors 220a and 220b can respectively be structurally identical to the sensor 220 from the first exemplary embodiment, and can consequently likewise in each case have an array of photodiodes arranged along a detection direction of the sensors 220a and 220b, respectively.

The sensors 220a and 220b can be embodied as position sensors for detecting the position of the optical element 130. In this case, the detection direction of the sensor 220a is arranged orthogonally with respect to the detection direction of the sensor 220b, wherein the detection direction of the sensor 220a is the y-direction and the detection direction of the sensor 220b is the x-direction. Furthermore, each of the two sensors 220a and 220b is assigned an encoder pattern on the optical element 130. These encoder patterns are respectively arranged opposite the sensors 220a and 220b. Consequently, the sensor 220a, with the aid of the encoder pattern arranged opposite to it, detects a displacement of the optical element 130 in the y-direction, and the sensor 220b, with the aid of the encoder pattern arranged opposite to it, detects a displacement of the optical element 130 in the x-direction.

In a similar manner to the sensor of the first exemplary embodiment, the detection direction of the sensor 220a is arranged orthogonally with respect to the expansion direction at the location of the detection region 225a. This ensures that the measurement is influenced as little as possible by the temperature-dictated expansion of the sensor receptacle 210. Furthermore, the detection region 225b of the sensor 220b is arranged at the temperature-invariant point 217 or in the temperature-invariant region of the sensor receptacle 210. This ensures that, upon a temperature-dictated expansion of the sensor receptacle 210, the position of the detection region 225b does not experience any change with respect to the measuring frame 140 serving as reference. In other words, upon homogeneous heating of the sensor receptacle 210, the position of both sensors 220a and 220b does not change in the detection direction.

What is advantageous about this embodiment is that two sensors 220a and 220b are fitted on a sensor receptacle 210. This simplifies the mounting of the sensors provided in the lithography apparatus 100, since it is merely necessary to align just one sensor receptacle 210 with respect to the measuring frame 140. Furthermore, a space-saving arrangement is thus made possible.

In a modification (not illustrated more specifically) of this exemplary embodiment, the sensors 220a and 220b are arranged on the sensor receptacle in such a way that neither the detection region 225a of the sensor 220a nor the detection region 225b of the sensor 220b is situated at the temperature-invariant point 217. Such a configuration results, for example, if the sensor 220b in FIG. 7 is displaced in the y-direction on the sensor receptacle 210. Since the detection direction of the sensor 220b is the x-direction, in this case as well the detection direction of the sensor 220b is orthogonal with respect to the expansion direction at the location of the detection region 225b, such that measurement errors on account of the temperature-dictated expansion of the sensor receptacle 210 are minimized. In this case, the detection directions of the sensors 220a and 220b need not necessarily be orthogonal with respect to one another. Rather, arrangements are also conceivable in which the detection directions of the sensors 220a and 220b are arranged at an angle of not equal to 90° with respect to one another, wherein the detection directions of the sensors 220a and 220b in each case correspond to the direction of the tangents of the expansion lines 216 at the location of the respective detection region 225.

It should be taken into consideration that the embodiments described above are merely by way of example and can be varied diversely within the context of the scope of protection of the patent claims.

Thus, it is also possible, for example to arrange more than two sensors on a sensor receptacle. By way of example, a plurality of sensors having the same detection direction can be provided for reasons of redundancy. Furthermore, it is conceivable to arrange two sensors having a parallel or antiparallel detection direction on a sensor receptacle and to realize a rotation sensor via corresponding evaluation of the sensor signals.

Furthermore, the sensor principle indicated above is merely by way of example and other sensor principles are also possible which are used to detect a physical quantity in at least one detection direction. Thus, it is also possible to provide an arrangement comprising a light transmitter and receiver instead of a sensor that detects an encoder pattern on the optical element. In the case of such an arrangement, by way of example, a laser fixedly connected to the measuring frame can emit a light ray that is reflected from a mirror provided on the optical element and is detected by the detection region of the sensor. In this case, the location of the incidence of the reflected light on the detection region changes depending on the position of the optical element relative to the measuring frame. In this case, too, the sensor is therefore characterized by a detection direction, wherein the location of incidence along the detection direction contains information about the position of the optical element with regard to one degree of freedom.

Further configurational possibilities for the sensor are laser interferometers and capacitive sensors which are likewise characterized by a detection direction.

LIST OF REFERENCE SYMBOLS

100 Lithography apparatus
110 Baseplate
120 Holding frame
130 Optical element
132 Encoder pattern
134 Pattern region
140 Measuring frame
160 Wafer receptacle
170 Wafer
180 Illumination apparatus
190 Mask
200 Sensor arrangement
210 Sensor receptacle
211 Baseplate
213 Leaf springs
215 Thickenings
216a . . . 216d Expansion lines
217 Temperature-invariant point
220, 220a, 220b Sensor
225, 225a, 225b Detection region
230 Evaluation device
240 Actuator
250 Sensor

The invention claimed is:

1. An apparatus, comprising:
a structural element;
a sensor having a detection region configured to detect a physical quantity in a detection direction with respect to the structural element; and
a sensor receptacle which mounts the sensor to the structural element,
wherein:
the sensor is arranged so that, upon a change in a temperature of the sensor receptacle, a maximum displacement of the detection region in the detection direction is less than what a maximum displacement of the detection region in the detection direction would be if the sensor were in a different arrangement in which the sensor and the detection direction were rotated by 90°;
a coefficient of thermal expansion of the sensor receptacle is different from a coefficient of thermal expansion of the structural element; and
the apparatus is a lithography apparatus.

2. The apparatus of claim 1, wherein the arrangement of the sensor is configured so that, upon a change in a temperature of the sensor receptacle, a maximum displacement of the detection region in the detection direction is less than what a maximum displacement in the detection direction would be if the sensor were in a different arrangement in which the sensor and the detection direction were rotated.

3. The apparatus of claim 1, wherein the arrangement of the sensor is configured so that the detection direction is substantially orthogonal to a thermal expansion direction of the sensor receptacle at the detection region of the sensor upon a change in the temperature of the sensor receptacle.

4. The apparatus of claim 1, comprising:
a first sensor having a first detection region configured to detect a physical quantity in a first detection direction; and
a second sensor having a second detection region configured to detect a physical quantity in a second detection direction,
wherein:
the first sensor is configured so that, upon a change in a temperature of the sensor receptacle by a predetermined temperature change value, the first detection region is substantially not displaced in the first detection direction; and
the second sensor is configured so that, upon a change in the temperature of the sensor receptacle by a predetermined temperature change value, the second detection region is substantially not displaced in the second detection direction.

5. The apparatus of claim 4, wherein the first detection direction is substantially orthogonal to the second detection direction.

6. The apparatus of claim 4, wherein:
the first sensor is arranged in a first region of the sensor receptacle; and
upon the change in the temperature by the predetermined temperature change value, the first region of the sensor receptacle is not displaced in any direction by more than a predetermined absolute value of expansion relative to the structural element.

7. The apparatus of claim 6, wherein:
the second sensor is arranged in a second region of the sensor receptacle; and
upon the change in the temperature by the predetermined temperature change value, the second region of the sensor receptacle is not displaced in any direction by more than a predetermined absolute value of expansion relative to the structural element.

8. The apparatus of claim 1, wherein:
the sensor is configured to detect a physical quantity in two detection directions;
the sensor is arranged at a position of the sensor receptacle; and
upon a change in the temperature by a predetermined temperature change value, the position of the sensor receptacle is not displaced in any direction by more than a predetermined absolute value of expansion relative to the structural element.

9. The apparatus of claim 1, wherein the sensor is configured so that, upon a change in the temperature of the sensor receptacle by 10 mK, the detection region is displaced in the detection direction by not more than 100 nm.

10. The apparatus of claim 1, wherein the coefficient of thermal expansion of the sensor receptacle is greater than the coefficient of thermal expansion of the structural element.

11. The apparatus of claim 1, further comprising spring elements which fix the sensor receptacle to the structural element.

12. The apparatus of claim 1, wherein the sensor receptacle is thermally decoupled from the structural element.

13. The apparatus of claim 1, wherein the structural element is a measuring frame.

14. The apparatus of claim 1, wherein the sensor is configured to detect the position of an optical element of the apparatus.

15. The apparatus of claim 1, wherein the sensor comprises a photodetector.

16. The apparatus of claim 1, comprising an illumination apparatus.

17. The apparatus of claim 16, wherein the illumination apparatus is configured so that, during use of the apparatus, the illumination apparatus generates a radiation beam which is capable of interacting with a mask and then passing through the lens.

18. The apparatus of claim 1, wherein the sensor is configured so that, upon a change in a temperature of the sensor receptacle, a displacement of the detection region in the detection direction is not greater than a displacement of the detection region in a direction orthogonal to the detection direction.

19. An apparatus, comprising:

a structural element;

a sensor having a detection region configured to detect a physical quantity in a detection direction with respect to the structural element; and a sensor receptacle which mounts the sensor to the structural element, wherein:
the sensor is arranged so that upon a change in a temperature of the sensor receptacle, a maximum displacement of the detection region in the detection direction is:
not greater than what a maximum displacement of the detection region in the detection direction would be if the sensor were in an arrangement in which the sensor and the detection direction were rotated by 90 °; and
less than what a maximum displacement in the detection direction would be if the sensor were in a different arrangement in which the detection direction were rotated; and
the apparatus is a lithography apparatus.

20. An apparatus, comprising:

a structural element;

a first sensor having a first detection region configured to detect a physical quantity in a first detection direction with respect to the structural element;

a second sensor having a second detection region configured to detect a physical quantity in a second detection direction with respect to the structural element; and a sensor receptacle which mounts the sensor to the structural element, wherein:
the first sensor is arranged so that, upon a change in a temperature of the sensor receptacle, a maximum displacement of the first detection region in the first detection direction is not greater than what a maximum displacement of the first detection region in the first detection direction would be if the sensor were in a different arrangement in which the sensor and detection direction were rotated by 90°; and
the apparatus is a lithography apparatus.

* * * * *